(12) United States Patent
Fleming

(10) Patent No.: US 6,503,409 B1
(45) Date of Patent: Jan. 7, 2003

(54) LITHOGRAPHIC FABRICATION OF NANOAPERTURES

(75) Inventor: James G. Fleming, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/579,824

(22) Filed: May 25, 2000

(51) Int. Cl.[7] ................................................ C03C 15/00
(52) U.S. Cl. ................................. 216/56; 216/2; 216/62; 216/72; 216/97
(58) Field of Search .................... 216/2, 38, 56, 216/62, 72, 97

(56) References Cited

U.S. PATENT DOCUMENTS

| | | | | |
|---|---|---|---|---|
| 5,462,467 A | * | 10/1995 | Macaulay et al. ............ 216/11 |
| 5,681,484 A | * | 10/1997 | Zanzucchi et al. ............. 216/2 |
| 5,855,801 A | * | 1/1999 | Lin et al. ....................... 216/2 |
| 5,985,164 A | * | 11/1999 | Chu et al. ................... 210/490 |
| 6,033,583 A | * | 3/2000 | Musket et al. ................ 216/56 |
| 6,044,981 A | * | 4/2000 | Chu et al. ................... 210/490 |
| 6,046,111 A | * | 4/2000 | Robinson .................... 156/345 |
| 6,087,274 A | * | 7/2000 | Tonucci et al. ............... 216/54 |
| 6,204,202 B1 | * | 3/2001 | Leung et al. ............... 438/778 |

* cited by examiner

Primary Examiner—Randy Gulakowski
Assistant Examiner—J Smetana
(74) Attorney, Agent, or Firm—Brian W. Dodson

(57) ABSTRACT

A new class of silicon-based lithographically defined nanoapertures and processes for their fabrication using conventional silicon microprocessing technology have been invented. The new ability to create and control such structures should significantly extend our ability to design and implement chemically selective devices and processes.

25 Claims, 5 Drawing Sheets

FIG. 5A
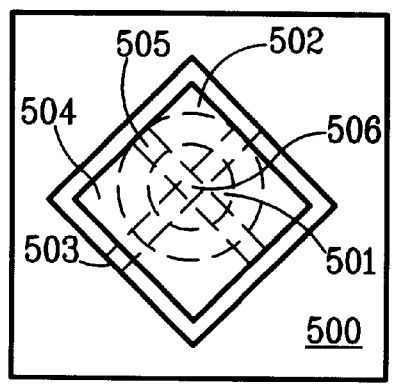
FIG. 5B
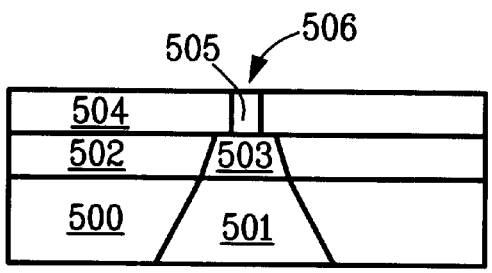
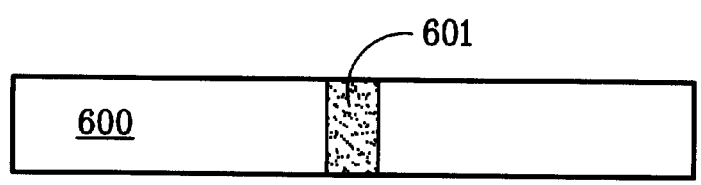
FIG. 6A
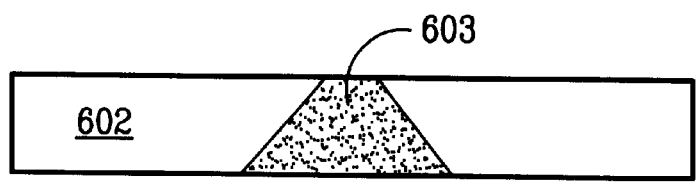
FIG. 6B
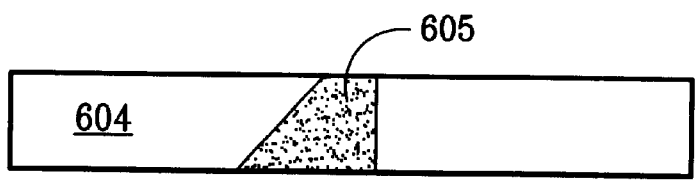
FIG. 6C
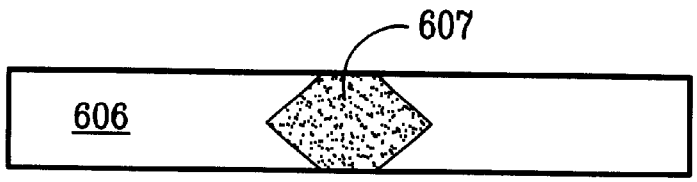
FIG. 6D
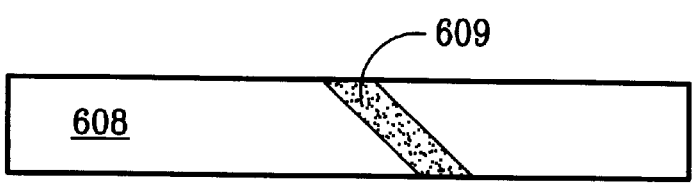
FIG. 6E

LITHOGRAPHIC FABRICATION OF NANOAPERTURES

GOVERNMENT RIGHTS

This invention was made with Government support under Contract DE-AC04-94AL85000 awarded by the U.S. Department of Energy. The Government has certain rights in the invention.

FIELD OF THE INVENTION

The present invention relates generally to nanometer-scale apertures and new techniques for fabrication thereof.

BACKGROUND OF THE INVENTION

Nanometer-scale pores, channels, and slits (collectively called nanoapertures herein) have a variety of physical and chemical properties which can make them useful in a variety of applications. Examples include separation of chemical, isomeric, or isotopic species, control of surface diffusion, electrokinetic fluidic devices, and DNA sequencing. Suitable nanopores and nanochannels must have shapes which are defined and fabricated with dimensions typically of a few nanometers, with tolerances of a nanometer or less, and chemical specificity at the atomic level. This is necessary so that the proper types of interaction take place between the structure of the nanopore or nanochannel and the atomic or molecular entities involved. Such interactions can take the form of "wetting" or "non-wetting" down to the level of sub-molecular moieties. Thus, nanopores and nanochannels can be made sensitive to not only the size, but also the shape and chemical structure of molecules. DNA sequencing will be used as a recent illustration of the utility of nanopores. Sequencing of the DNA molecule offers tremendous promise for medical and biotechnological applications of the future. To allow routine diagnostic use of this technique, however, it will be necessary to greatly decrease the time and expense required to decode a particular strand of DNA.

A new approach to DNA sequencing is being developed. The principle is to pull a single strand of double-stranded DNA through a miniscule aperture. An ionic current is used to pull the DNA strand. The DNA unzips one base pair at a time as the single strand threads through the aperture. As a result, when they pass through the aperture, they block the aperture in a manner characteristic of their molecular shape and local charge densities. A reduction thus appears in the ionic current which is characteristic of the molecular species passing through the aperture.

DNA has four base pairs, the amino acids adenine, thymine, guanine, and cytosine. Because these base pairs have different sizes and shapes, the amount of blockage observed is different for each species of base pair. By monitoring the current as the DNA strand is pulled through the aperture, direct sensing of the composition and ordering of the DNA strand can be accomplished.

The sequencing technique described above is still in the earliest stages of development, but offers promise for sequencing base pairs at a rate perhaps as high as 1000 base pairs per second. A practical apparatus with a reasonable amount of parallelism could then read an entire human genome in less than a day. This data could then be searched and decoded to reveal a wide range of genetic traits, including hereditary diseases, genetic tendencies toward disease and genetically-determined metabolic factors relative to pharmacological therapeutical choices.

Initial studies were based on the use of organic ion channels as the sequencing aperture. Ion channels are the "pores" in cellular membranes which regulate the flow of chemicals in and out of the cell. In particular, a channel called alpha haemolysin was used. The effective diameter of such ion channels is about 1.5 nm.

A cell membrane comprising such a channel was used to separate two compartments containing a potassium ion solution. When DNA strands were introduced into one of the compartments, they took on a negative charge under the conditions there extant. When a voltage was applied across the two compartments, the voltage dragged the charged DNA strand through the ion channel. The associated current showed the expected variations as the base pairs transited the ion channel.

Organic ion channels, however, have proven too delicate for use in a real gene sequencer—the haemolysin channels are quickly damaged by the stressful interactions involved. Additionally, the high compliance of the molecular structure of the ion channels reduces the distinctness of the signals characterizing the various base pairs. It was rapidly realized that a better choice would be a nanometer-scale aperture, or "nanopore", made of some durable, hard, probably nonorganic material.

Unfortunately, there are no routine and controllable techniques available to fabricate such nanopores. Conventional technology can at best produce holes with diameters of 40–50 nm, whereas the requirement for a sequencing nanopore is roughly 2 nm.

A crude technique has been introduced to make small holes in silicon nitride. Schematically, this technique uses ion beam etching to make a shallow curved depression on each side of a substrate material, increasing the depth of the second depression until the two depressions meet, and thereby forming a small hole through the substrate. This technique has successfully been used to make holes as small as 4 nm, but the results of this type of process are extremely fragile, and also quite variable in nanopore size and shape.

There is a clear need for a technique to fabricate nanopores suitable for DNA sequencing, and for the product of such technique. The present invention enables fabrication of suitable nanopores in a silicon substrate by novel combination of well-known, controllable, and compatible microelectronic fabrication processes.

SUMMARY OF THE INVENTION

Techniques to fabricate nanoapertures with characteristic dimensions as small as 1–2 nm using novel silicon lithographic techniques has been developed. This is the only known technique to form apertures of this size. Such apertures are important for development of new approaches to DNA sequencing, and for other applications involving electronic, ionic, and molecular tunneling.

BRIEF DESCRIPTION OF THE DRAWINGS

FIG. 5. Schematic illustration of a nanopore aperture formed through a substrate fabricated using the instant invention.

FIG. 6. Schematic illustration of various trench cross-sections which can be produced using the instant invention.

DETAILED DESCRIPTION

Figure 1A:
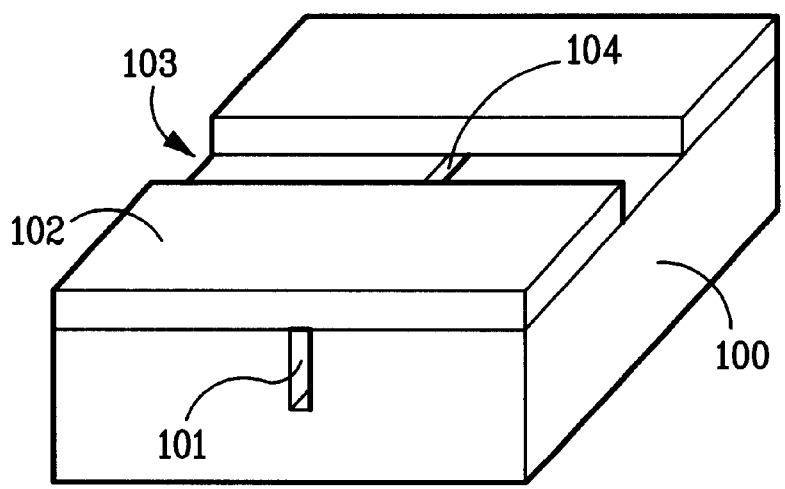
FIG. 1. Schematic illustrations of various types of nanoapertures.
Figure 1B:
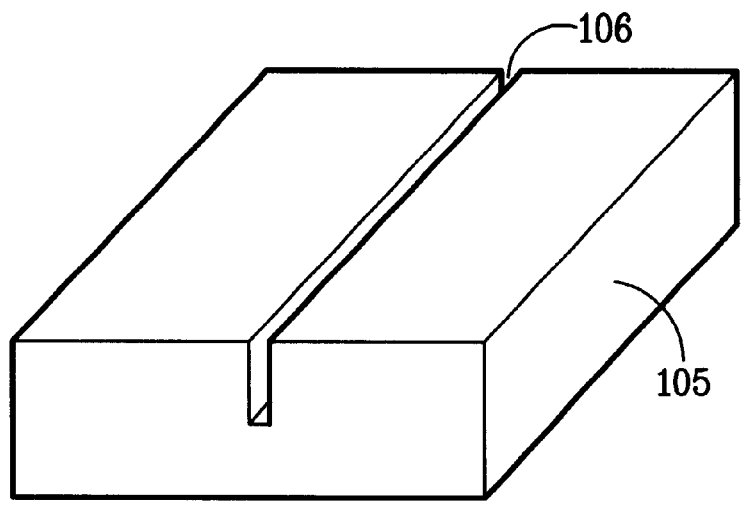
Figure 1C:
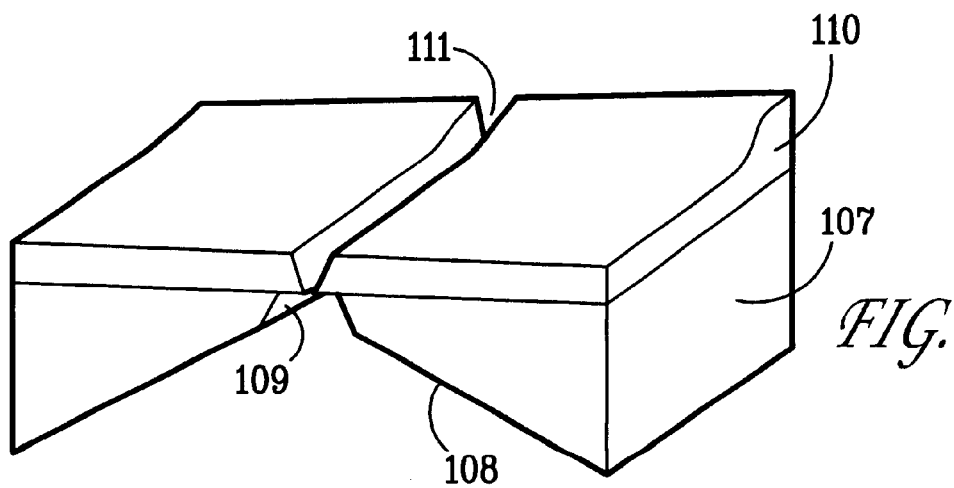

Nanoapertures is a term comprising nanopores, nanochannels, and nanoslits, as shown in FIGS. 1a, 1b, and 1c respectively.

FIG. 1a shows a nanopore after the instant invention. A nanochannel 101 is fabricated in substrate layer 100. A second layer 102 is formed on top of substrate layer 100, and a second nanochannel 103 is fabricated in second layer 102. Here the two nanochannels are shown to be at right angles, so that a rectangular hole 104 joins the two nanochannels at their intersection.

FIG. 1b shows an isolated nanochannel 106 fabricated in a substrate layer 105. Techniques for such fabrication will be described later.

FIG. 1c shows a penetrating nanoslit. Substrate 107 is thinned from beneath by etch 108, and then is opened along a narrow region under the nanoslit 111 which is fabricated in the second layer 110. This structure allows the extremely thin second layer (typically less than 100 nm) sufficient structural support despite the opening in the substrate.

Such nanoapertures may penetrate the structure on which they reside, as shown in FIG. 1c, or not, as in FIGS. 1a and 1b. The common tie between these structures is that they each possess a hollow structural feature whose size can be as small as a few nanometers, or even one nanometer. Such structures interact directly with atoms and molecules in interesting and useful ways, but are difficult to fabricate so that the desired effect can be obtained.

As described earlier, nanopores have a new and special place if DNA sequencing. The following discussion will center on the fabrication of a nanopore according to the instant invention which is suitable for DNA sequencing.

A major problem to be overcome in the fabrication of nanopores for use in DNA sequencing is the miniscule size of the aperture required—nominally 2 nm or less in all dimensions. That is, all three lateral dimensions characterizing the nanopore must be on the order of a few nanometers.

Figure 2A:
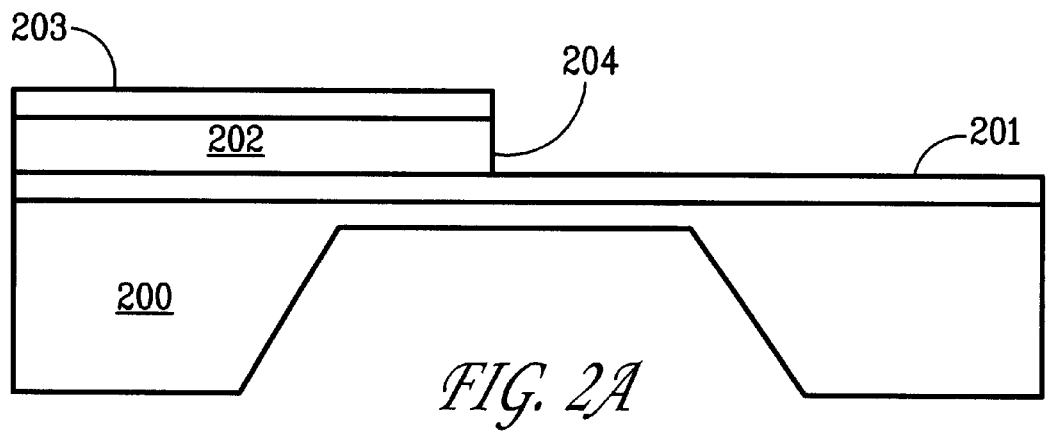
FIG. 2. Schematic illustration of intermediate structures formed during fabrication of a nanopore using the instant invention.

Intermediate structures formed during one implementation of this technique is shown schematically in FIG. 2. FIG. 2a shows a silicon substrate 200 which has grown on its top surface a thin (few nm) SiN base layer 201, a thin (~5–10nm) Si layer 202, and a thin (few nm) SiN stop layer 203. This stack of layers has been patterned and etched so that the two top layers 202 and 203 are removed, leaving an exposed edge 204 of silicon. Layers 201 and 203 can alternately be made of $SiO_2$. The back surface of the silicon substrate 200 can be locally thinned as shown to make opening of the aperture easier.

Figure 2B:
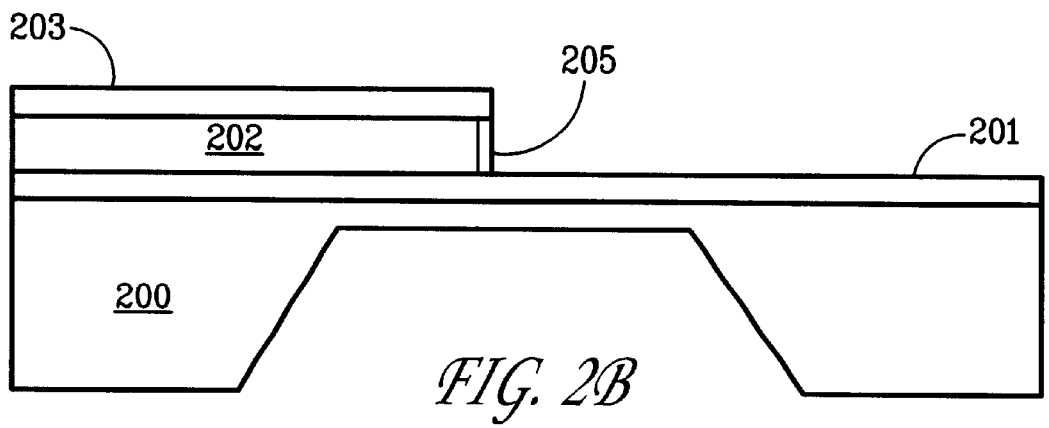

In the next step, the exposed silicon edge 204 is oxidized, forming a thin (2–5 nm) fillet 205 of silicon oxide, as shown in FIG. 2b. Fillet 205 is one of a pair of structures which will determine the ultimate dimensions of the aperture. Although various approaches toward fillet fabrication are known, they have the common factor that an out-of-plane structure with very small lateral dimensions is formed by defining the out-of-plane structure in a first material, growing or depositing a thin layer of a fillet material thereon, and removing excess material. The result is an out-of-plane fillet made of the fillet material where at least one dimension is roughly the thickness of said thin layer. This allows features with a characteristic dimension as small as one nanometer to be reliably fabricated.

Next, a layer of polysilicon 206 is deposited on the top surface of substrate 200 and the elements in place thereon. This layer is thicker than the combined height of layers 202 and 203, so that layer 203 lies below the lowest point of the polysilicon surface. The surface is now planarized, using chemical-mechanical polishing or equivalent techniques, said polishing being carried out so that the process stops when the SiN stop etch layer 203 is reached. At this point (FIG. 2c), the SiN layer 203 is stripped, the structure is polished to restore flatness, and a new, very thin (~1 nm) SiN layer 207 is grown or deposited on the newly flattened surface.

Now the second structure which will define the size and character of the aperture is formed. The earlier steps are repeated, with SiN layer 207 substituting for the SiN base layer 201. A silicon layer is grown atop SiN layer 207, and a second SiN stop etch layer atop that. These layers are again patterned and etched to leave a second exposed edge of silicon. The second exposed edge is oriented at an angle (here shown as perpendicular) to the first edge 204.

Figure 3A:
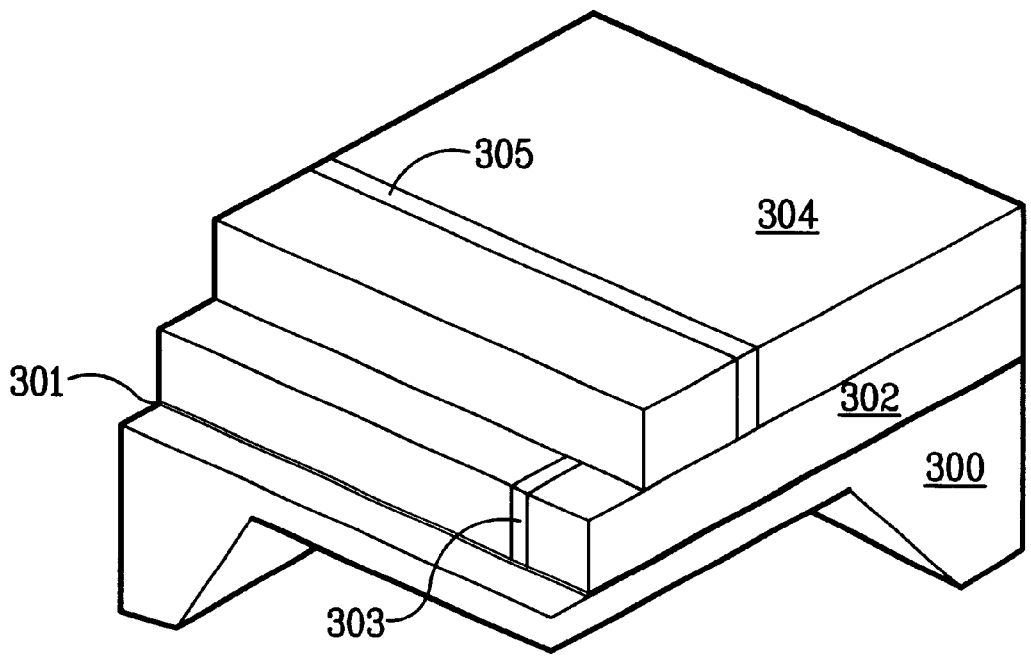
FIG. 3. Schematic illustration of later intermediate structures formed during fabrication of a nanopore using the instant invention.

The structure as it appears when the second oxide fillet is formed and the surface is planarized is shown in FIG. 3a. Here 300 is the thinned silicon substrate, 301 is a thin SiN base layer, 302 is a first silicon structural layer, 303 is a first oxide fillet embedded in layer 302, 304 is a second silicon structural layer, and 305 is a second oxide fillet embedded in layer 304, and oriented roughly at right angles to fillet 303.

Figure 3B:
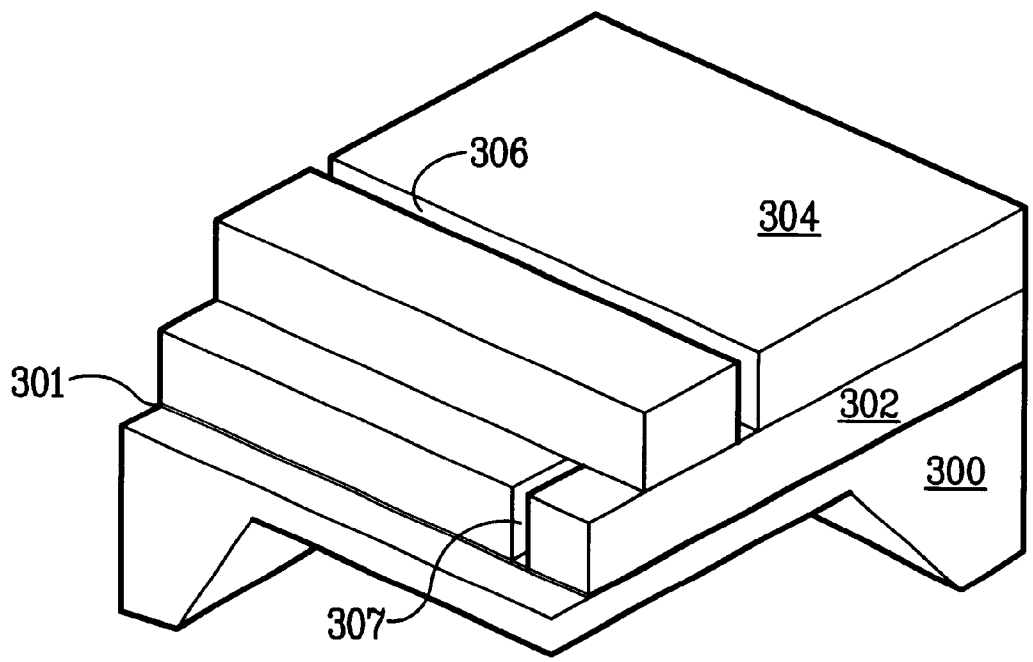

To form the aperture, it is sufficient to remove the oxide with a hydrofluoric acid etch. This yields the structure shown in FIG. 3b, where trenches 306 and 307 replace oxide fillets 303 and 305. The aperture appears at the point of intersection of the two trenches, and opens a passage between the two trenches whose size and shape is determined by the trenches.

There are many approaches toward altering the aperture and its surroundings. Some of these are shown schematically in FIG. 4, while others will be clear to one familiar with silicon microprocessing. All are intended to be included within the scope of this invention.

Figure 4:
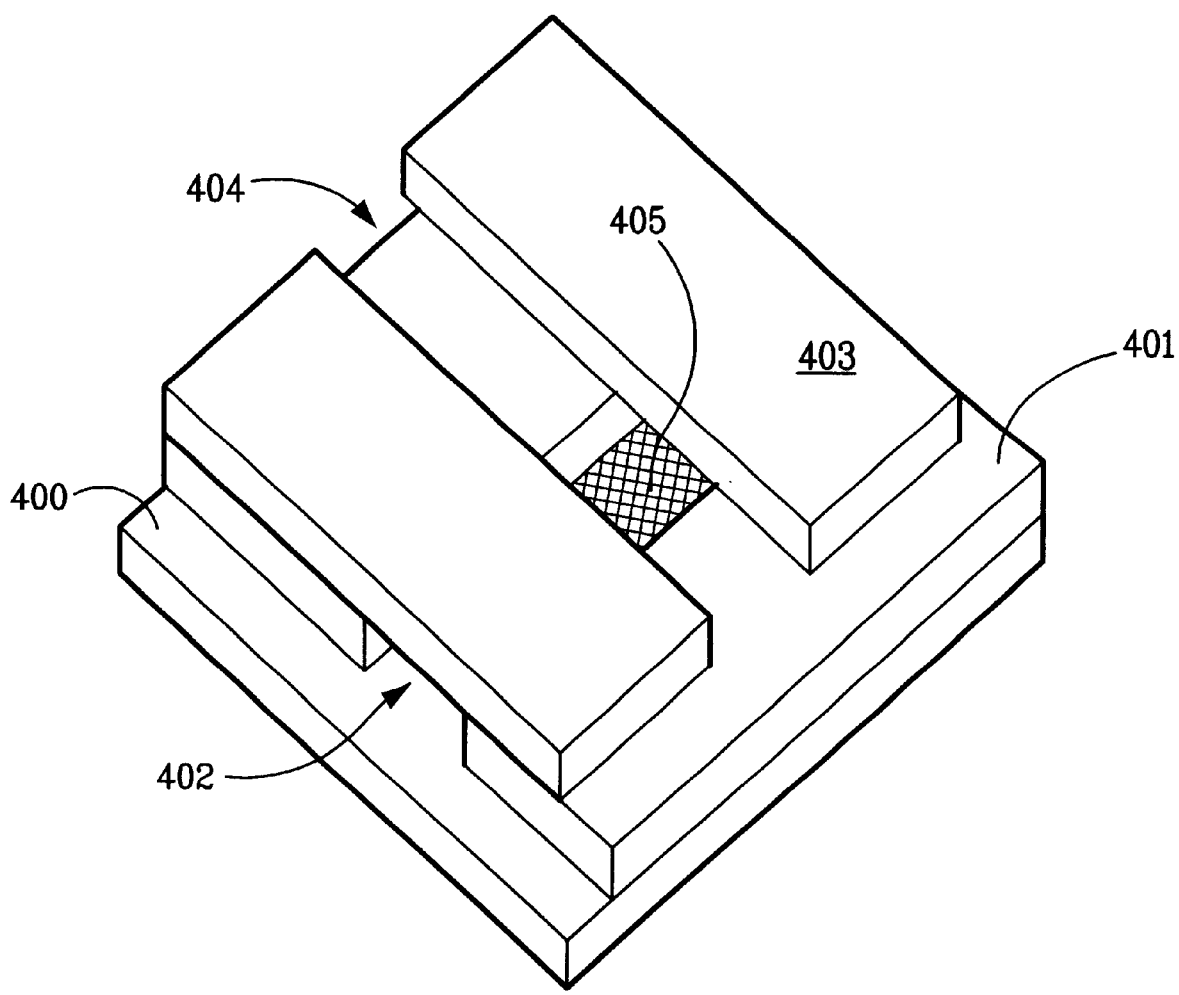
FIG. 4. Schematic illustration of a nanopore aperture formed between two trenches fabricated using the instant invention.

FIG. 4 shows the aperture formed by the procedure described above. 400 is the thinned substrate, 401 is the first silicon structural layer, 402 is the first trench, 403 is the second structural layer, 404 is the second trench, and 405 (the cross-hatched region) marks the aperture between the trenches. This aperture is nominally a rectangle (assuming that the trenches are perpendicular) having width equal to the width of first trench 402 and length equal to the width of second trench 404. In this structure aperture 405 opens a passage between first trench 402 and the volume above the structure. Note that if it is desired to reduce the size of the aperture 405 further, this can be accomplished by oxidizing the silicon, thus causing the walls of the trenches to grow toward each other.

It is possible to open an aperture between the two sides of the substrate. FIG. 5 shows one approach to accomplish this. FIG. 5a shows a top view, and FIG. 5b shows a cross-section. After the first silicon structural layer 502 and its oxide fillet (not shown), and the second silicon structural layer 504 and its oxide fillet (not shown) are formed, but prior to removal of the oxide fillets by etching with hydrofluoric acid, a hole 501 is opened in the thinned region of the substrate under the intersection of the oxide fillets by masking and etching. Exposure of the structure to a hydrofluoric acid etch then removes the oxide from the second oxide fillet to form second trench 505. However, owing to the limited exposure time, only a local area of oxide near the intersection point is removed from the first oxide fillet, thereby opening void 503. At this point aperture 506 extends from one side of the structure to the other, with the smallest dimension being defined by the intersection of the oxide fillets. Such an opening can also be opened from the top side of the structure using, e.g., reactive ion etching or selective wet etching.

The size and nature of the aperture can be tailored for specific purposes by using combinations of materials, crystalline orientations, and selective material removal techniques which are well known in the art. Some of the possibilities are indicated in FIG. 6. FIG. 6a shows trench 601 generated in structural layer 600 with the nominally rectangular cross-section produced by the earlier procedure. FIG. 6b shows structural layer 602 with a quadrilateral trench 603 generated therein by an etching procedure without perpendicular selectivity. FIG. 6c shows structural layer 604 with a combination trench 605 as might be generated using the procedure described in detail earlier if a non-perpendicular etching technique were used before growing the oxide fillet. FIG. 6d shows structural layer 606 with a trench 607 having a hexagonal cross section, which again can be made using selective etching. FIG. 6e shows structural layer 608 with a slanting trench 609 which can be fabricated using reactive ion etching. These are a small sample of the trench cross-sections which can be produced using selective etching techniques and proper choice of materials in the instant invention.

Once formed, it is possible to alter the surface properties of the aperture and the surrounding structures by depositing thin surface layers, or by adsorbing material onto the surface. Such modifications will change the selectivity of the aperture when used for DNA sequencing.

The above implementation of the instant invention makes a number of implicit and explicit assumptions, which do not form intrinsic limitations to the use of the fabrication techniques or to the form of their product. For example, it was assumed that the first and second channel are oriented perpendicularly on the surface, thus producing a nanopore with nominally rectangular periphery. This orientation is not driven by the materials being used, as first silicon edge 204 and the second silicon edge (not shown) need not be oriented in special manners relative to the crystallographic axes of silicon substrate 200, even though such orientation can allow smaller and more precisely defined structures to be built. As a result, the nanopore can be fabricated with nearly unlimited cross-sectional shape.

Similarly, the above implementation shows the production of vertical fillets, and channels with vertical walls. By proper choice of substrate crystalline orientation and selective etches, the fillets can be grown at a nonnormal angle relative to the substrate surface. These and other variations will be clear to one skilled in silicon microfabrication.

Figure 2C:
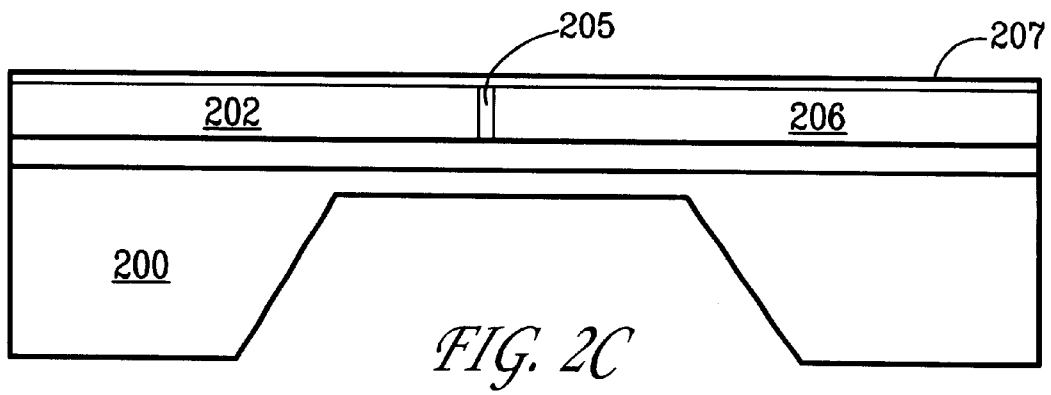

Similar techniques can be used to produce other nanostructures. For example, if the structure shown in FIG. 2c is subjected to a hydrofluoric acid etch, the result will be a nanochannel of the type shown in FIG. 1b, with a channel width approximately equal to the width of the oxide fillet 205. If the substrate of a nanochannel is relieved behind the nanochannel as shown in FIG. 4, a nanoslit can be formed piercing the substrate. Related nanostructures can easily be formed using variations of the techniques which comprise the instant invention.

The description of the instant invention in the specification is based on specific implementations thereof, and are not intended to limit the scope of the invention. The scope is intended to be set only by the claims as interpreted in light of the specification and the figures.

I claim:

1. A process to fabricate nanopores, comprising the steps of:
   a) fabricating a first fillet of a first material on a silicon substrate;
   b) embedding said fillet in a second material;
   c) planarizing said second material, creating thereby a second surface;
   d) fabricating a second fillet of the first material on said second surface, so that a projected intersection of the first fillet and the second fillet falls onto the silicon substrate; and,
   e) removing the first and second fillets by etching.

2. The process of claim 1, wherein said first material comprises silicon oxide.

3. The process of claim 1, wherein said second material comprises polysilicon.

4. The process of claim 1, wherein said planarizing is carried out by steps including chemical-mechanical polishing.

5. The process of claim 1, wherein said removing the first and second fillets is accomplished by selective etching techniques.

6. The process of claim 5, wherein said selective etching techniques comprise a hydrofluoric acid etching step.

7. The process of claim 1, further comprising the step of opening a hole through the silicon substrate beneath the projected intersection of the first and second fillets.

8. The process of claim 7, wherein opening a hole is carried out by steps comprising etching.

9. A process to fabricate nanopores, comprising the steps of:
   a) forming a first structural layer on a substrate;
   b) forming a first etchable fillet within the first structural layer;
   c) forming a second structural layer atop the first structural layer;
   d) forming a second etchable fillet within the second structural layer, said second etchable fillet crossing the first etchable fillet at a nonzero angle and forming an intersection therebetween; and
   e) etching sufficient material from the first etchable fillet and from the second etchable fillet to form an aperture at the intersection.

10. The process of claim 9, wherein the first and second etchable fillets comprise silicon oxides.

11. The process of claim 10, wherein said step of etching sufficient material comprises a hydrofluoric acid etching step.

12. The process of claim 9, wherein the first and second structural layers comprise polysilicon.

13. The process of claim 9, wherein the substrate is thinned in a region directly under the intersection of the first and second etchable fillets.

14. The process of claim 9, wherein the step of etching material from the etchable fillets removes substantially all the material of the first and second etchable fillets.

15. The process of claim 9, wherein the steps of forming the first structural layer and of forming the first etchable layer within the first structural layer are carried out by actions comprising:
   a) depositing a first layer of silicon on the substrate;
   b) patterning and etching said first layer so as to produce an edge in the desired location of said first etchable fillet;

c) growing a thin silicon oxide layer on said edge;

d) covering said edge with a polysilicon layer.

16. The process of claim 15, wherein said actions further comprise the step of chemical-mechanical polishing to planarize the polysilicon layer.

17. The process of claim 9, wherein the steps of forming the second structural layer and of forming the second etchable layer within the second structural layer are carried out by actions comprising:

e) depositing a prelayer of silicon atop the first structural layer;

f) patterning and etching said prelayer so as to produce an edge in the desired location of said second etchable fillet;

g) growing a thin silicon oxide layer on said edge;

h) covering said edge with a polysilicon layer.

18. The process of claim 17, wherein said actions further comprise the step of chemical-mechanical polishing to planarize the polysilicon layer.

19. The process of claim 9, wherein said step or etching sufficient material comprises a reactive ion etching step.

20. The process of claim 9, further comprising opening a passage through the substrate by steps including etchants exposure.

21. The process of claim 20, wherein said etchants exposure is carried out by processes comprising reactive ion etching.

22. The process of claim 20, wherein said etchants exposure is carried out by processes comprising wet etching.

23. The process of claim 20, wherein said passage is directly under the intersection of the first and second etchable fillet.

24. The process of claim 9, further comprising the step of narrowing the aperture by steps comprising oxidizing the aperture walls.

25. The process of claim 9, further comprising the step of modifying the surface chemistry of the aperture by depositing a surface layer of chemicals thereon.

* * * * *